(12) United States Patent
Redington

(10) Patent No.: US 10,994,093 B1
(45) Date of Patent: May 4, 2021

(54) WEARABLE THERAPEUTIC HAND POUCH

(71) Applicant: Allison Redington, Dunlap, IL (US)

(72) Inventor: Allison Redington, Dunlap, IL (US)

( * ) Notice: Subject to any disclaimer, the term of this patent is extended or adjusted under 35 U.S.C. 154(b) by 0 days.

(21) Appl. No.: 17/071,410

(22) Filed: Oct. 15, 2020

Related U.S. Application Data

(60) Provisional application No. 62/989,745, filed on Mar. 15, 2020.

(51) Int. Cl.
*A61M 21/02* (2006.01)
*A61M 21/00* (2006.01)

(52) U.S. Cl.
CPC ..... *A61M 21/02* (2013.01); *A61M 2021/0022* (2013.01); *A61M 2205/0216* (2013.01)

(58) Field of Classification Search
CPC . A63B 23/16; A63B 21/0004; A63B 21/0442; A63B 71/148; A63B 71/145; A61H 2205/065; A61H 39/04; A61H 2201/1635; A61H 2201/165; A61H 2201/1695; A61H 7/003; A61H 99/00; A41D 13/084; A41D 13/088; A41D 19/0017; A41D 19/0048; A41D 2400/32; A41D 2400/322
See application file for complete search history.

(56) References Cited

U.S. PATENT DOCUMENTS

2008/0271224 A1* 11/2008 Wilbert ............ A41D 19/01523
2/161.1

OTHER PUBLICATIONS https://www.amazon.com/dp/B008E378RI/ref=pe_175190_21431760_M3T1_ST1_dp_1—accessed Dec. 17, 2020 (Year: 2013).*
Invoice for Venum gloves (Year: 2013).*

\* cited by examiner

*Primary Examiner* — Christine H Matthews
*Assistant Examiner* — Joshua Daryl D Lannu
(74) *Attorney, Agent, or Firm* — Dale J. Ream

(57) ABSTRACT

The present invention is a therapeutic hand pouch assembly which through deep pressure therapy provides calm and soothing effects to the wearer. The assembly has a main body that includes an outer layer of fabric and defines an interior of gel, foam, glass beads, or combinations thereof. The assembly includes opposed straps or elastic bands having adjustment options so as to be wearable on a person's hand. Such assembly is inexpensive, durable, washable, portable, fully protective and ideally adapted to provide an improved experience to a user of any age under stress conditions.

18 Claims, 3 Drawing Sheets

WEARABLE THERAPEUTIC HAND POUCH

REFERENCE TO RELATED APPLICATIONS

This application claims the priority of provisional patent application U.S. Ser. No. 62/989,745 filed Mar. 15, 2020 titled STRESSLET and which is incorporated in its entirety herein by reference.

BACKGROUND OF THE INVENTION

Field of the Invention

This invention relates generally to a stress relieving pouch formed on deep pressure therapy, and more particularly to a therapeutic hand pouch which can be worn on palm and finger where user can apply pressure while feeling stressed, anxious or overloaded.

Description of the Related Art

In people, anxiety can interfere with the body's physiological ability to process information. When constant worry and stress make a person's heart race, it can be hard to concentrate, relax or even fall asleep. The body is a complex machine with many moving parts. When a person can't fully process the world around him, it can affect just about every part of life.

Deep Pressure Stimulation (DPS) is firm but gentle squeezing, hugs, or holding that relaxes the nervous system. Harvard researchers and others have found that firm, gentle and consistent pressure on the body can make people with autism and sensory processing disorder feel calmer, more relaxed and less anxious. This pressure can be applied with the hands, special massage tools, or products that your child can wear or wrap around themselves to provide pressure. Done properly, this therapy triggers a chain reaction in the body that releases an overall sense of calm and peace.

There are multiple solutions that have been found in prior art focusing on stress relieving mechanisms. For instance, therapy apparel for children diagnosed with sensory integration dysfunction bearing U.S. Pat. No. 6,401,249B2 issued to Virginia Tech Intellectual Properties Inc, Kansas State University. The patent discloses a therapy apparel is provided to assist in therapy sessions with children diagnosed with sensory integration dysfunction and impaired motor development. The apparel includes a fabric top to be worn over the shoulders and trunk of a child, together with a cape and close-fitting headgear. The top has fanciful theme decorations (e.g., a beetle) and is equipped with a series of flexible elastic straps for the feet, knees and hands of the child and which can be used during a therapy session. The cape is likewise theme-decorated and includes handholds allowing the child to spread the cape during imaginative play. The headgear is constructed using padded side and sections with flexible elastic sections between the sections, and a chin strap allowing the headgear to be drawn into close conforming relationship with the child's head. A series of individual accouterments can be placed on the headgear at the discretion of the child.

U.S. Pat. No. 7,601,045B2 disclosing therapeutic hand toys are issued to Tangle Inc. The invention provides systems and methods for a textured therapeutic toy that can be manipulated into an infinite number of shapes and configurations. The invention is best applied to relieve minor stress as well as strengthen hand muscles, rehabilitate finger and joint movement and improve overall range of hand motion. In one exemplary embodiment, a textured coating is applied to the surface of each segment that gives the therapeutic toy a unique feel, thereby creating a pleasant sensation and feel to the hands and fingers.

Segmented ball with lighted elements bearing U.S. Pat. No. 7,867,115B2 is issued to Tangle Inc. Embodiments of the instant invention include lighted bounceable toys for play and amusement. Such toys or structures can be made in an infinite number of graceful and useful configurations. Exemplary bounceable ball toys include a light assembly having a power source and a plurality of light emitting elements, and a spherical skeletal structure having a plurality of segments. The spherical skeletal structure defines an open interior cavity, and at least some segments of the skeletal structure include a channel opening that faces toward the interior cavity. Light emitting elements transmit light to the channel openings.

A therapeutic appliance for stress relief bearing US patent 2,007,025,6333A1 is issued to Wolf Owen M Jr. The patent discloses a massage foot gear enabling wearer to have relaxation and therapeutic massage while performing normal walking motion. Continuation of research (medical and technical) to incorporate automatic, non-invasive stimulation of atrophied limbs and trunk areas through impulse nodes implanted in flexible wraps. Target meridian points (as in reflexology) in the foot area, to enhance the feeling of wellbeing as well as possible therapy for diseases related to this area. Wraps will also target atrophied muscular areas to increase muscle dexterity and circulation, possibly therapeutic for MS patients as well as sport therapies and accident related injuries.

A weighted blanket bearing French patent 201,200,973, 9A1 is issued to Linda Collier. A weighted blanket comprising a cover and a body adapted to be inserted into the cover, wherein the body contains a plurality of cells which are filled with a gel, so as to provide weight to the body.

Another patent on Therapeutic hand toys bearing worldwide patent 2,006,019564A3 is issued to Richard E Zawitz. The invention provides systems and methods for a textured therapeutic toy that can be manipulated into an infinite number of shapes and configurations. The invention is best applied to relieve minor stress as well as strengthen hand muscles, rehabilitate finger and joint movement and improve overall range of hand motion. In one exemplary embodiment, a textured coating is applied to the surface of each segment that gives the therapeutic toy a unique feel, thereby creating a pleasant sensation and feel to the hands and fingers.

There are multiple solutions that have been presented in prior art. However, these solutions are limited and restricted to their conventional systems. The current invention is focused on presenting an assembly which is based on deep pressure. Deep pressure is a therapy where touch or weight is used to help people who have sensory sensitivity. It uses pressure via touch to help someone who may need an intervention if they're feeling stressed, anxious or overloaded. The product is made out of fabric on the outside and foam on the inside where the strap keeps the product properly aligned on the hand/fingers. Furthermore, the pouch can have Velcro and metal loop, so that a user can tighten it to his/her desirable pressure.

None of the previous inventions and patents, whether considered singly or in combination, is seen to describe the instant invention as claimed. Therefore, it would be desirable to have a wearable therapeutic hand pouch that overcomes, resolves, and surmounts the aforementioned shortcomings of prior art.

SUMMARY OF THE INVENTION

In light of the disadvantages of the prior art, the following summary is provided to facilitate an understanding of some of the innovative features unique to the present invention and is not intended to be a full description. A full appreciation of the various aspects of the invention can be gained by taking the entire specification, claims, drawings, and abstract as a whole.

Stress relief is critical. In our frenetic modern world, stress is a near constant fact of life for many. Between the demands of work life, personal life, and distressing world events, the need for stress relief products and methods is at an all-time high. Learning to manage stress effectively is vital to positive long-term health outcomes, both mental and physical.

There are multiple cases of stress. For instance, stress during medical procedures is a truth which can't be denied. Whether a patient is young or elderly stress during treatment is an integral part. The medical word for this anxiety of going under the knife is tomophobia, which translates to "fear of surgery." Anxiety becomes a psychological issue when your fear of surgery is so significant that you may begin to have physical symptoms like a racing heart, nausea, and chest pain. A severe bout of anxiety is commonly known as a panic attack and can be caused when someone who is afraid of surgery dwells on their fear. Patients with an anxiety disorder may be more prone to surgical anxiety and fear that the average patient, but many people first experience anxiety when they're preparing for medical procedure.

Another case of stress is in children. It is a common phenomenon today in children that they lack consistency and concentration. They are restless and a seven-hour day of learning further stresses them out. Their behavior matched their frustration and became increasingly disruptive. Stress balls had been disallowed in her school due to the fact that most kids cannot handle any type of ball in the classroom! Past experience proved this as they were usually thrown, passed, or used to hit other students, which inevitably ended with the teacher losing her calm and yelling at them to put the balls away.

The current invention in its preferred embodiment presents a product which is like a stress ball. The proposed assembly is in the form of a pouch which can be worn on a person's hand. The exterior surface made out of fabric and has a stress relieving foam or gels beads interiorly. The Velcro™ strap keeps the product tightened on the hand/fingers. It has tightening mechanism which can be including but not limited to elastic or Velcro™ or metal loop, so a user can tighten it to desirable pressure. The product is further proposed to be made of other materials which can be thicker or leathery fabric or similar material. Furthermore, it is also proposed to provide beads or gel in interior body of stress ball. The Velcro™ strap could have other methods of tightening and securing, for instance metal snap buttons, elastic, a clasp, and the like.

The product in its further embodiment provides an opening for the index finger. The index finger opening secures the product more to the hand and also it provides pressure to the hand which is comforting for the wearer. The invention provides "Deep Pressure Therapy" where touch or weight is used to help people who have sensory sensitivity. It uses pressure via touch to help someone who may need an intervention if they're feeling stressed, anxious or overloaded.

The assembly as per preferred embodiment applies deep pressure therapy/stimulation to the palm, fingers and thumb. The user can readjust the Velcro™ to tighten or loosen the strap and pressure to individual's ease.

The product as per further embodiment can be used for adults and children facing stress, anxiety, fear, autism, sensory disorders, obsessive compulsive disorder and much more. The product size can be adjusted if it were to be used by a child versus an adult.

A primary object of the present invention is to provide a therapeutic hand pouch that is wearable on a person's hand.

Another object of the present invention is to provide a therapeutic hand pouch, as aforesaid, that is based on deep pressure therapy.

Another object of the present invention is to provide a therapeutic hand pouch, as aforesaid, which applies deep pressure therapy/stimulation to the fingers and thumb of a human user's hand.

Still another object of the present invention is to provide a therapeutic hand pouch, as aforesaid, that helps to calm people when they are overstimulated, and to strengthen them when they are scared or nervous.

A further object of the present invention is to provide a therapeutic hand pouch, as aforesaid, which has fabric covering on its outer side and forms an interior cavity that may include foam or foam beads, shredded foam, or gel beads. Furthermore, it can have elastic band, hook and loop fasteners, or metal loops, so a user can tighten the body portion about a user' wrist and finger, respectively, to their desirable pressure.

It is also the object of the invention to include a squeezable foam which allows better squeezing and soothing to the user.

A particular object of the present invention is to provide a therapeutic hand pouch, as aforesaid, where user can adjust the pressure and firmness on the hand by loosening or tightening the strap on the fingers/hand.

Another specific object of the present invention is to provide a therapeutic hand pouch, as aforesaid, which can be suitable for users of all age and gender.

Another specific object of the present invention is to provide a therapeutic hand pouch, as aforesaid, that is easy to use and convenient to the user.

Another specific object of the present invention is to provide a therapeutic hand pouch, as aforesaid, that is attractive and comes in multiple sizes, colors, and designs.

Another specific object of the present invention is to provide a therapeutic hand pouch, as aforesaid, that is portable and cost effective.

Another specific object of the present invention is to provide a therapeutic hand pouch, as aforesaid, that provides a wearable deep pressure therapy stress ball.

Other aspects, advantages and novel features of the present invention will become apparent from the detailed description of the invention when considered in conjunction with the accompanying drawings.

This summary is provided merely for purposes of summarizing some example embodiments, so as to provide a basic understanding of some aspects of the subject matter described herein. Accordingly, it will be appreciated that the above-described features are merely examples and should not be construed to narrow the scope or spirit of the subject matter described herein in any way. Other features, aspects, and advantages of the subject matter described herein will become apparent from the following Detailed Description, Figures, and Claims.

DESCRIPTION OF THE PREFERRED EMBODIMENT

Figure 1:
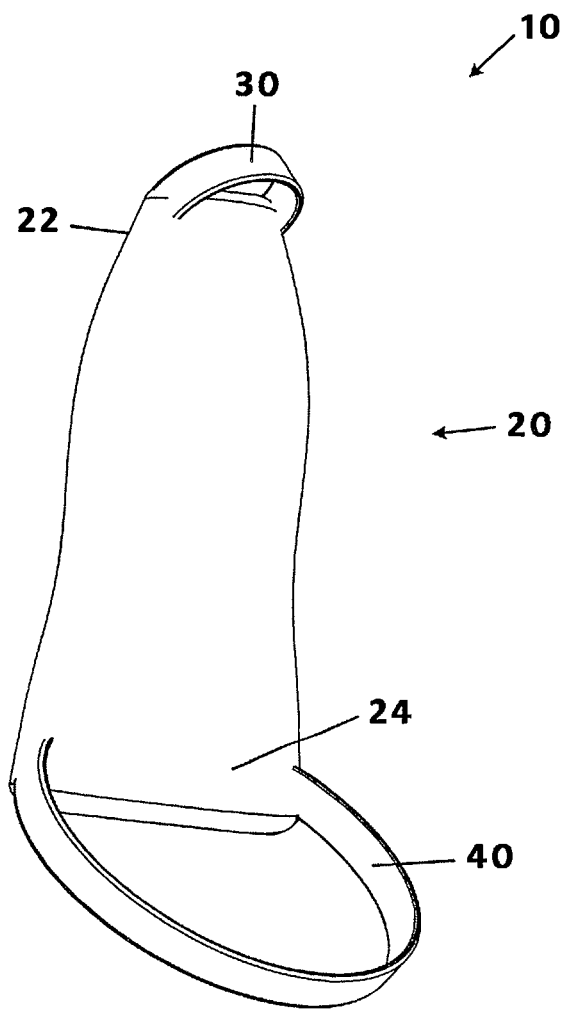
FIG. 1 is a perspective view of a wearable therapeutic device according to a preferred embodiment of the present invention.
Figure 2A:
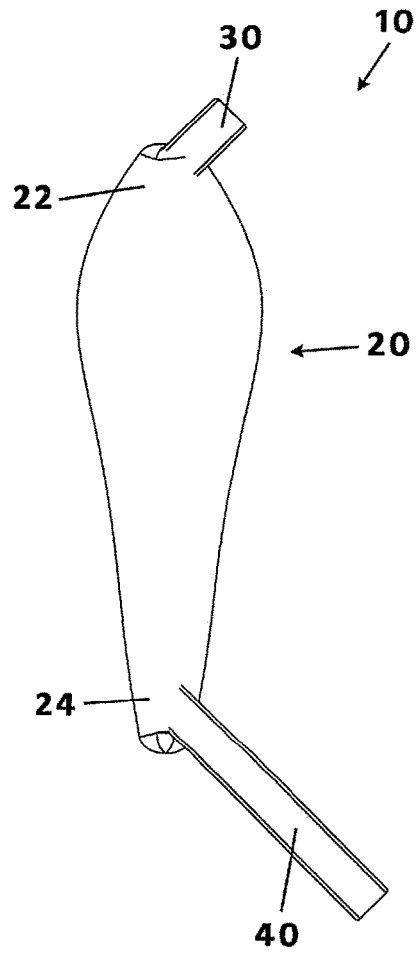
FIG. 2a is a side view of the wearable therapeutic device as in FIG. 1.
Figure 2B:
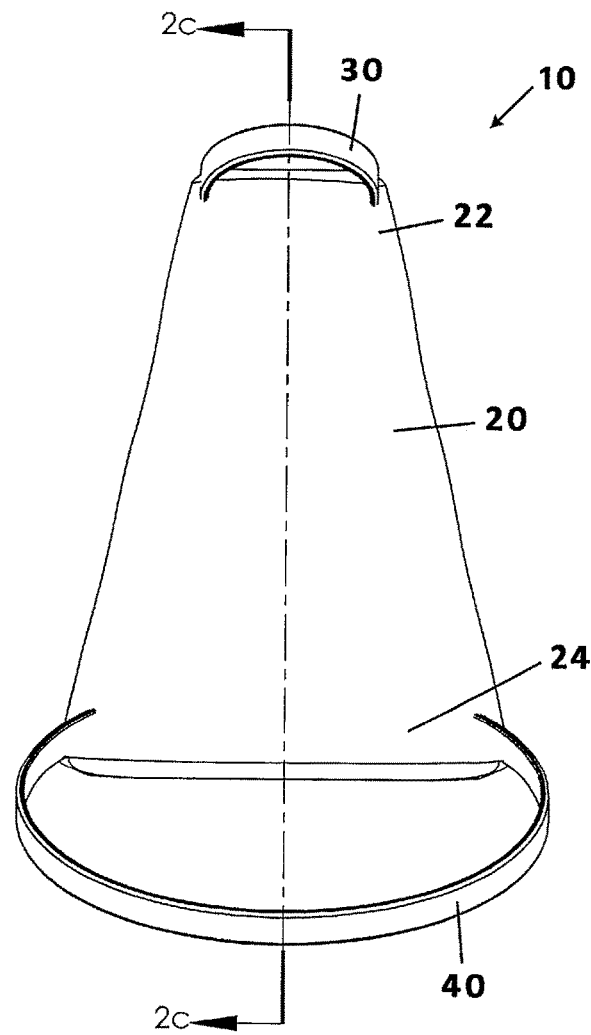
FIG. 2b is a front view of the wearable therapeutic device as in FIG. 1.
Figure 2C:
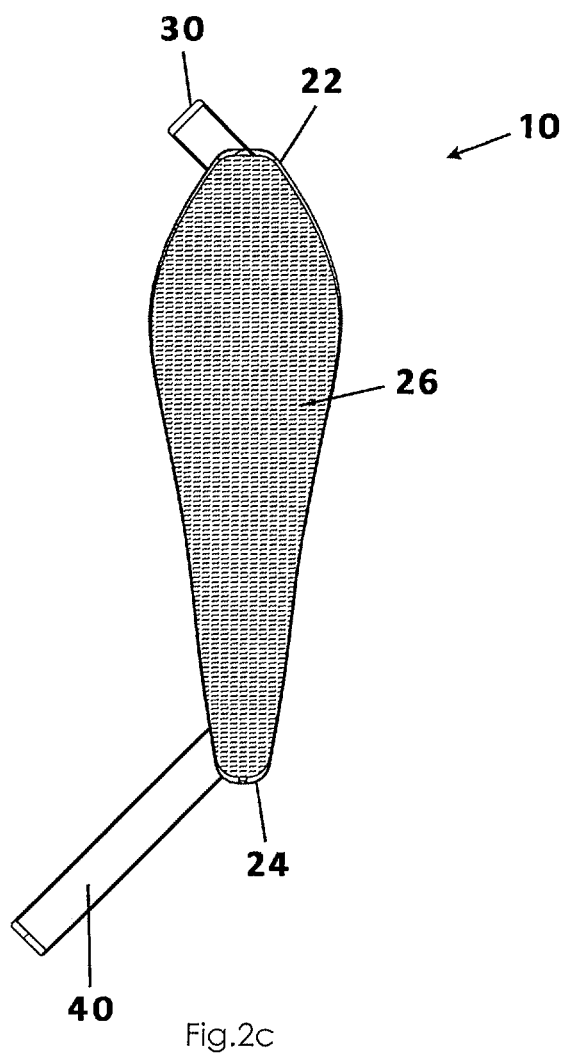
FIG. 2c is a sectional view taken along line 2c-2c of FIG. 2b.

A wearable therapeutic hand pouch according to a preferred embodiment of the present invention will be described in detail with reference to FIGS. 1 to 2c of the accompanying drawings. Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

The wearable therapeutic hand pouch 10 according to the present invention includes a body member 20, a first fastener 30, and a second fastener 40. Specifically, the body member 20 has a first end 22 and a second end 24 opposite the first end 22. The body member 20 may be constructed of a fabric material that is pliable or, in other words, squeezable, and resilient. In an embodiment, the exterior of the body member 20 may be constructed of leather or textured fabric. The body member 20 may include a front panel and a rear panel coupled together—such as along respective peripheral edges—that, together, form what may be referred to as a midsection and which, together, define closed interior area, also referred to as an interior cavity or just a cavity. The midsection extends substantially between the first and second ends.

The body portion 20 is pliable and squeezable because a spongy material 26 is disposed in the interior area. The sponge or spongy material 26 enables the body portion to have a deep pressure sensory stimulation effect on a wearer's palm, thumb, and fingers. The material situated in the interior area may include one of foam, shredded foam, or foam beads. In an embodiment, the sponge-like material may include gel or gel beads. Accordingly, the body portion 20 may be referred to as a deep pressure sensory device.

In another aspect, the body portion 20 is aligned and held in place by fasteners coupled to the opposed ends of the body member 20 that are configured to receive a finger and wrist of a wearer's hand. More particularly, a first fastener 30 may include opposite ends coupled to the first end 22 of the body portion 20, the first fastener 30 configured in the form of a loop that defines a void configured to receive a wearer's wrist therethrough. In other words, the wearable therapeutic hand pouch 10 may be secured and worn on the wrist of a person. Similarly, a second fastener 40 may include opposite ends coupled to the second end 24 of the body portion 20, the second fastener 40 configured in the form of a loop that defines a void configured to receive a wearer's finger (such as an index finger) therethrough.

Preferably, the loops of the first fastener 30 and second fastener 40 are elastic bands that are operable to be resilient and to self-tighten to a wearer's wrist. In other embodiments, however, the fasteners 30, 40 may be a strap, clasp, snap combination, hook and loop fastener, or the like having means for manually tightening or loosening the fasteners 30, 40 as desired. For instance, a user may desire to adjust the tightness of the fasteners 30, 40 and, thus, the amount of deep pressure the body member 20 exerts on the palm of a wear's hand. In all of these embodiments, each fastener has an adjustable length and, therefore, tightness.

With further regard to the fasteners (straps), the second fastener 40 (i.e. the second loop) defines a diameter that is larger than a diameter defined by the first fastener 30 (i.e. first loop). This is because the second fastener 40 is large enough to receive a wearer's wrist whereas the first fastener 30 is merely large enough to receive a finger of a wearer.

Similarly, the width of the body member 20 may not be uniform throughout between the opposed ends. In other words, the distance between side edges of the body member 20 proximate the first end 22 may be shorter than the distance between side edges of the body member 20 proximate the second end 24 (FIG. 2b). In other words, the body member 20 may have a frusto-rectangular configuration to accommodate the size of a wearer's wrist and to align appropriately in the wearer's palm. With this geometry, the body member 20 has a circumference that is increasing between the first end 22 and second end 24.

Having described the invention in detail, those skilled in the art will appreciate that modifications may be made to the invention without departing from its spirit. The particular shape or configuration of the platform or the interior configuration may be changed to suit the system or equipment with which it is used. Therefore, it is not intended that the scope of the invention be limited to the specific embodiment illustrated and described. Rather, it is intended that the scope of this invention be determined by the appended claims and their equivalents.

I claim:

1. A wearable therapeutic hand pouch, comprising:
    a body member having a first end and a second end opposite said first end and having a front side and rear side coupled together peripherally so as to extend between said first and second ends, said body member having a pliable outer material that defines a closed interior area that is filled with a sponge material;
    a first fastener extending away from said first end that is configured to receive a wearer's finger; and
    a second fastener extending away from said second end that is configured to receive a wearer's wrist;
    wherein said first end of said body member defines a width that is smaller than a width defined by said second end of said body member such that said body member has an increasing circumference between said first end and said second end.

2. The wearable therapeutic hand pouch as in claim 1, wherein:
    said first fastener is a loop defining an opening and constructed of elastic material; and
    said second fastener is a loop defining an opening and constructed of elastic material.

3. The wearable therapeutic hand pouch as in claim 2, wherein said loop associated with said second fastener has a diameter greater than a diameter of said loop associated with said first fastener.

4. The wearable therapeutic hand pouch as in claim 1, wherein said sponge material includes foam, shredded foam, or foam beads.

5. The wearable therapeutic hand pouch as in claim 1, wherein said material includes gel or gel beads.

6. The wearable therapeutic hand pouch as in claim 1, wherein an exterior surface of said body member is constructed of leather or textured fabric.

7. The wearable therapeutic hand pouch as in claim 1, wherein said body member is configured to align with a palm of a wearer's hand when said first fastener is associated with the wearer's index finger and said second fastener is associated with the wearer's wrist.

8. A wearable therapeutic hand pouch, comprising:
- a body member having a first end and a second end opposite said first end and having a front side and rear side coupled together peripherally so as to extend between said first and second ends, said body member having a pliable outer material that defines a closed interior area that is filled with a sponge material;
- a first fastener extending away from said first end that is configured to receive a wearer's finger; and
- a second fastener extending away from said second end that is configured to receive a wearer's wrist;
- wherein said first fastener and said second fastener have an adjustable length.

9. The wearable therapeutic hand pouch as in claim 8, wherein said body member is a deep pressure sensory device.

10. A wearable therapeutic hand pouch, comprising:
- a body member having a first end and a second end opposite said first end and having a pliable mid-section that extends between said first and second ends, said mid-section defining a closed interior area that is filled with a sponge material;
- a first fastener having opposed ends coupled to said first end and that forms a loop that is configured to receive a wearer's finger; and
- a second fastener having opposed ends coupled to said first end and that forms a loop that is configured to receive a wearer's wrist;
- wherein said first end of said body member defines a width that is smaller than a width defined by said second end of said body member such that said body member has an increasing circumference between said first end and said second end.

11. The wearable therapeutic hand pouch as in claim 10, wherein:
- said first fastener is constructed of an elastic material; and
- said second fastener is constructed of an elastic material.

12. The wearable therapeutic hand pouch as in claim 10, wherein said loop associated with said second fastener has a diameter greater than a diameter of said loop associated with said first fastener.

13. The wearable therapeutic hand pouch as in claim 10, wherein said sponge material includes foam, shredded foam, or foam beads.

14. The wearable therapeutic hand pouch as in claim 10, wherein said sponge material includes gel or gel beads.

15. The wearable therapeutic hand pouch as in claim 10, wherein an exterior surface of said body member is constructed of leather or textured fabric.

16. The wearable therapeutic hand pouch as in claim 10, wherein said body member is configured to align with a palm of a wearer's hand when said first fastener is associated with the wearer's index finger and said second fastener is associated with the wearer's wrist.

17. The wearable therapeutic hand pouch as in claim 10, wherein said body member is a deep pressure sensory device.

18. A wearable therapeutic hand pouch, comprising:
- a body member having a first end and a second end opposite said first end and having a pliable mid-section that extends between said first and second ends, said mid-section defining a closed interior area that is filled with a sponge material;
- a first fastener having opposed ends coupled to said first end and that forms a loop that is configured to receive a wearer's finger; and
- a second fastener having opposed ends coupled to said first end and that forms a loop that is configured to receive a wearer's wrist;
- wherein said first fastener and said second fastener have an adjustable length.

\* \* \* \* \*